United States Patent
Goutsis

(10) Patent No.: US 10,322,075 B2
(45) Date of Patent: Jun. 18, 2019

(54) COLOURING AGENT FOR KERATIN FIBRES, COMPRISING A SELECTED DYE AND A POLYOL

(71) Applicant: Henkel AG & Co. KGaA, Duesseldorf (DE)

(72) Inventor: Konstantin Goutsis, Juechen (DE)

(73) Assignee: Henkel AG & Co. KGaA, Dusseldorf (DE)

( * ) Notice: Subject to any disclaimer, the term of this patent is extended or adjusted under 35 U.S.C. 154(b) by 0 days.

(21) Appl. No.: 15/554,650

(22) PCT Filed: Mar. 3, 2016

(86) PCT No.: PCT/EP2016/054557
§ 371 (c)(1),
(2) Date: Aug. 30, 2017

(87) PCT Pub. No.: WO2016/142269
PCT Pub. Date: Sep. 15, 2016

(65) Prior Publication Data
US 2018/0235856 A1 Aug. 23, 2018

(30) Foreign Application Priority Data
Mar. 12, 2015 (DE) .................... 10 2015 204 471

(51) Int. Cl.
*A61Q 5/10* (2006.01)
*A61K 8/34* (2006.01)
*A61K 8/39* (2006.01)
*A61K 8/41* (2006.01)
*A61Q 5/06* (2006.01)

(52) U.S. Cl.
CPC .............. *A61K 8/345* (2013.01); *A61K 8/342* (2013.01); *A61K 8/39* (2013.01); *A61K 8/411* (2013.01); *A61K 8/418* (2013.01); *A61Q 5/065* (2013.01); *A61K 2800/4322* (2013.01)

(58) Field of Classification Search
CPC .......... A61K 8/342; A61K 8/345; A61K 8/39; A61K 8/418; A61K 2800/4322; A61Q 5/065

See application file for complete search history.

(56) References Cited

U.S. PATENT DOCUMENTS

| 2013/0269121 A1* | 10/2013 | Pratt | A61K 8/492 8/407 |
| 2015/0182441 A1* | 7/2015 | Goutsis | A61K 8/362 132/208 |

FOREIGN PATENT DOCUMENTS

| DE | 2151131 A1 | 4/1973 | |
| DE | 202008016408 U1 | 3/2009 | |
| DE | 10 2012 216606 A1 * | 3/2014 | ............. A61K 8/898 |
| WO | 9838976 A1 | 9/1998 | |
| WO | 2006013036 A1 | 2/2006 | |

OTHER PUBLICATIONS

Binary dyes combination to control yellow-orange after semipermanent straighteners (Feb. 6, 2016).*
EPO, International Search Report and Written Opinion issued in International Application No. PCT/EP2016/054557, dated Apr. 19, 2016.
"Binary dyes combination to control yellow-orange after semipermanent straighteners"; disclosed by Antonio Consoli and Katiuscia Grevalcuore by Alfaparf Group; published on Feb. 6, 2015.
"Hair dyeing composition", published on Jul. 15, 2009 in the IP.com Journal.

* cited by examiner

*Primary Examiner* — Eisa B Elhilo
(74) *Attorney, Agent, or Firm* — Lorenz & Kopf, LLP

(57) ABSTRACT

Agents for coloring keratinous fibers and methods of dying human hair are provided herein. In an embodiment, an agent is provided for coloring keratinous fibers. The agent is included in a cosmetic carrier and includes at least one non-ionic direct dye and at least about 0.1 wt. %—in relation to the entire agent—of one or several polyols.

19 Claims, No Drawings

COLOURING AGENT FOR KERATIN FIBRES, COMPRISING A SELECTED DYE AND A POLYOL

CROSS-REFERENCE TO RELATED APPLICATION

This application is a U.S. National-Stage entry under 35 U.S.C. § 371 based on International Application No. PCT/EP2016/054557, filed Mar. 3, 2016, which was published under PCT Article 21(2) and which claims priority to German Application No. 10 2015 204 471.8, filed Mar. 12, 2015, which are all hereby incorporated in their entirety by reference.

TECHNICAL FIELD

This application relates to compositions for dyeing keratinous fibers, in particular human hair, comprising a selected dye combined with a polyol. The present disclosure also relates to the use of the composition and to a method for dyeing keratinous fibers.

BACKGROUND

Either direct dyes or oxidation dyes are generally used for dyeing keratinous fibers. In the case of oxidation dyes, although it is possible to achieve intense coloring with good fastness properties, the oxidizing agents used to develop these colors, such as $H_2O_2$, can result in damage to the fibers in some cases. Furthermore, some oxidation dye precursors or specific mixtures of oxidation dye precursors can occasionally induce sensitization in people with sensitive skin. Direct dyes are applied with care. However, their disadvantage is that the colorings often have insufficient fastness, especially when the hair is washed, but also due to other influences such as sunlight or reactive environmental chemicals, such as swimming pool water.

In addition to insufficient fastness, the poor coverage of gray by direct dyes is another general disadvantage. Full coverage or concealment of gray hair is considered as perfect gray coverage. If a dyeing agent with optimal gray coverage is applied to a person whose hair is, for example, 50% gray (50% of the hair is gray and 50% of the hairs are still pigmented), after applying the dye, there is a uniform color result, i.e. no perceptible difference in color between the gray and non-gray hair after the dyeing.

While good to very good gray coverage can generally be achieved with oxidative dyes, the gray coverage with direct dyes is thus far not very satisfactory. Therefore, there are few alternatives available for laminating or covering their (wholly or partly) gray hair for users who wish to avoid using oxidative hair dye due to the associated hair damage.

In addition to beautiful hair color, users want shiny hair. Shiny hair looks attractive and healthy, and the hairstyle is perceived as well cared for and vital. In many cases, the consumer has multiple wishes they would like to fulfill simultaneously: they want an attractive hair color and shiny hair at the same time. For practical reasons, they would like their hair to undergo a single treatment only.

The state-of-the-art technology already offers various methods for dying the hair in the widest possible variety of shades. But as before, there is a demand for new coloring agents, which have a high color uptake of the dyes during the dyeing process, and at the same time enable good gray coverage and produce an exceptionally high gloss.

BRIEF SUMMARY

Agents for coloring keratinous fibers and methods of dying human hair are provided herein. In an embodiment, an agent is provided for coloring keratinous fibers. The agent is included in a cosmetic carrier and includes at least one non-ionic direct dye and at least about 0.1 wt. %—in relation to the entire agent—of one or several polyols.

In another embodiment, a method includes dying human hair using an agent. The agent is included in a cosmetic carrier and includes at least one non-ionic direct dye and at least about 0.1 wt. %—in relation to the entire agent—of one or several polyols.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The task of the present disclosure was therefore to prepare new dyeing agents based on direct dyes, which intensively dye the hair, provide good gray coverage and at the same time give it a lot of shine. The shine of the colors produced by these methods should be long-lasting and last several washes.

This problem was solved by an agent for coloring keratinous fibers, specifically human hair, containing in a cosmetic carrier
(a) at least one non-ionic direct dye
and
(b) at least about 0.1 wt. %—in relation to the entire agent—of one or several polyols.
It was found that agents containing at least one non-ionic direct dye and at least about 0.1 wt. %—in relation to the entire agent—of one or more polyols can dye keratinous fibers in intense shades. Surprisingly, it was found that at the same time as the coloring, the shine of keratinous fibers can be increased significantly and the gray coverage improved.

Keratinous fibers include pelts, wool, feathers and, in particular, human hair. Although the agents are particularly suitable for coloring keratinous fibers, there are no basic obstacles to their use in other fields.

The concept of dyeing agents for keratinous fibers means the keratinous fibers are dyed using direct dyes.

In addition, these agents can include oxidation dye precursors, so-called developers and coupler components. Developers and couplers diffuse separately in the keratinous fibers and produce the actual dyes under the influence of an alkalizing agent (for example, ammonia) and an oxidant (typically hydrogen peroxide) in chemical reaction with each other. The dyeing agents can also contain one or more oxidizing dyes. If the hair dyeing agents only contain direct dyes, the hair is dyed without being bleached at the same time. If the agents contain additional developers, couplers and/or oxidizers, the keratinous fibers are also bleached due to the additional oxidant it contains. Bleaching as well as coloring is explicitly encompassed in the definition of the coloring.

The agents contain the ingredients (a) and (b) in a cosmetic carrier, preferably in a suitable aqueous, alcoholic or aqueous alcoholic carrier. Carriers such as creams, emulsions, gels or tenside-containing, foaming solutions, such as shampoos, foaming aerosols, foam formulations or other preparations suitable for application on the hair, are used for dyeing the hair. However, it is also conceivable that the agents could be integrated in a powdery or a tablet-like formulation.

According to the present disclosure, anhydrous-alcoholic solutions are anhydrous solutions containing from about 3 to about 70 wt. % of a monovalent $C_1$-$C_4$ alcohol, particularly ethanol and/or isopropanol. The agents can also contain other organic solvents, such as methoxybutanol or benzyl alcohol. All water-soluble organic solvents are preferred. According to this present disclosure, the aqueous carrier contains at least about 30 wt. % of water, in particular, at least about 50 wt. % of water, based on the total weight of the agent. Aqueous carriers are preferred.

The first essential ingredient (a) contained by the agent is at least one non-ionic direct dye. This can be selected from the group HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, HC Blue 15, Disperse Blue 3, HC Violet 1, Disperse Violet 1, Disperse Violet 4, Disperse Black 9, 1,4-diamino-2-nitrobenzene, 2-amino-4-nitrophenol, 1,4-Bis(2-Hydroxy ethyl)-amino-2-nitrobenzene, 3-Nitro-4-(2-hydroxy ethyl) aminophenol, 2-(2-hydroxyethyl)amino-4,6-dinitrophenol, 4-[(2-hydroxyethyl)amino]-3-nitro-1-methyl benzene, 1-Amino-4-(2-hydroxyethyl)amino-5-chloro-2-nitrobenzene, 4-Amino-3-nitrophenol, 1-(2'-Ureidoethyl)amino-4-nitrobenzene, 2-[(4-Amino-2-nitrophenol)amino]benzoic acid, 4-[(3-hydroxypropyl)amino]-3-nitrophenol, 4-Nitro-o-phenylenediamine, 6-Nitro-1,2,3,4-tetrahydroquinoxaline, 2-hydroxy-1,4-naphthoquinone, picramic acid and their salts, 2-Amino-6-chloro-4-nitrophenol, 4-(Ethylamino)-3-nitrobenzoic acid and 2-Chlor-6-ethylamino-4-nitrophenol.

Particularly preferred non-ionic direct dyes are HC Blue 12 and HC Blue 15.

In a particularly preferred embodiment, the non-ionic direct dye used is HC Blue 12 using formula (I):

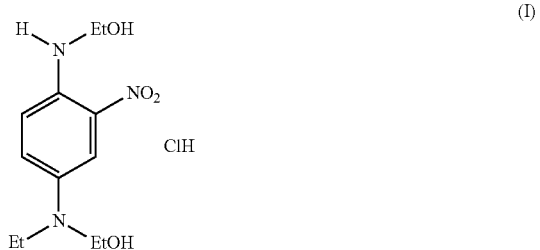

(I)

This particularly preferred dye is the hydrochloride of 2-[ethyl-4-[(2-hydroxyethyl)amino]-3-nitroanilino]ethanol.] The dye has CAS number 132885-85-9.

In a particularly preferred embodiment, the non-ionic direct dye used is HC Blue 15 using formula (II):

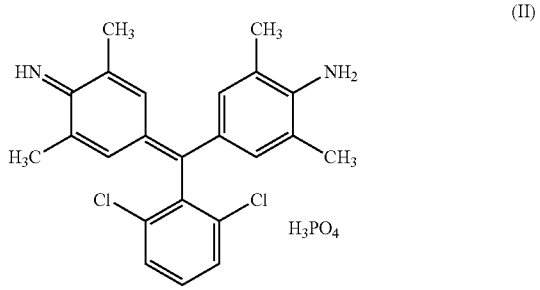

(II)

This particularly preferred direct non-ionic dye is a 1:1 mixture of phosphoric acid and 4-[(2,6-dichlorophenyl)(4-imino-3,5-dimethylcyclohexa-2,5-dien-1-ylidene)methyl]-2,6-xylidine, which is also known as CAS number 74578-10-2.

The agent for dyeing keratinous fibers can contain the non-ionic direct dye agents, in principle, in volumes of from about 0.01 to about 5.0 wt. %. It is possible to produce intense color results, shine and good gray coverage on the keratinous fibers in volumes under about 1.5 wt. %. Accordingly, it is further preferred that the nonionic direct dye(s) is/are contained in a volume of from about 0.05 to about 0.175 wt. %, and particularly preferred from about 0.075 to about 0.2 wt. %—in each case, in relation to the total weight of the agent.

The non-ionic direct dye used in combination with a polyol to dye keratinous fibers produce an intense color result and improve the shine of the fibers and the gray coverage. Here, an intense color, greatly increased shine and improved gray coverage was observed on the keratinous fibers, especially if the polyol(s) (b) were used in a minimum volume of about 0.1 wt. %.

As the second integral component (b), the agent therefore contains one or more polyol(s) in a total volume of at least about 0.1 wt. %. In this case, the calculation basis for the volume of polyols (b) is the total of all the polyols contained in the agent used in relation to the total volume of the agent.

Preferred polyols are multivalent $C_2$-$C_9$ alkanols with two to six hydroxyl groups and polyethylenglycole with from 3 to 20 ethylene oxide units. The agents contain at least one multivalent $C_2$-$C_9$-Alkanol with two to six hydroxyl groups or at least one water-soluble polyethylene glycol with from 3 to 20 ethylene oxide units, or mixtures of at least one multivalent $C_2$-$C_9$-alkanol with two to six hydroxyl groups and at least one water-soluble polyethylene glycol with from 3 to 20 ethylene oxide units.

Preferred are the $C_2$-$C_9$-alkanols with two to six hydroxyl groups selected from 1.2 propylene glycol, 1,3-propylene glycol, 2-methyl-1,3-propanediol, glycerol, 1,2-butylene glycol, 1.3 butylene glycol, 1,4-butylene glycol, 1,2-pentane diol 1,5-pentane diol, 1,2-hexanediol, 1,6-hexanediol, 1,2,6-Hexantriol, 1,2-octanol, 1,8-octanol, dipropylene glycol, tripropylenglycol, giglycerol, triglycerol, erythritol, sorbitol, cis-1,4-dimethylolcyclohexane, trans-1,4-dimethylolcyclohexane, any isomeric mixtures of cis and trans-1,4-dimethylolcyclohexane and mixtures of these polyols. Suitable water soluble polyethylene glycols are selected from PEG-3, PEG-4, PEG-6, PEG-7, PEG-8, PEG-9, PEG-10, PEG-12, PEG-14, PEG-16, PEG-18 and PEG-20 and mixtures thereof, such as PEG-3 to PEG-8 are preferred.

Other suitable polyols are methylol compounds, such as specifically trimethylolethane, trimethylolpropane, trimethylol butane, pentaerythritol and dipentaerythritol, sugar alcohols with from 5 to 12 carbon atoms, such as sorbitol or mannitol, sugar with from 5 to 12 carbon atoms such as glucose or sucrose or amino sugar such as glucamine.

Particularly preferred polyols are selected from the group of 1,2-propylene glycol, glycerol, 1,3-butylene glycol, PEG-3, PEG-4, PEG-5, PEG-6, PEG-7, PEG-8 and mixtures thereof. Particularly preferred polyols are 1,2 propylene glycol, 1,3 butylene glycol, PEG-8, or mixtures thereof.

Although even small volumes of 0.1 wt. % polyol lead to a more intense color, increased shine and improved gray coverage, the effects of a total volume of polyol(s) of at least 1.0 wt. % is particularly clear. The polyols are therefore preferred in a total volume of from about 1.0 to about 20.0 wt. %, preferably from about 1.5 to about 15.0 wt. % and more preferably from about 2.0 to about 10.0 wt. %.

The agents can contain at least one other direct dye in addition to the direct pulling dye(s) (a). More direct dyes can be selected from anionic or cationic direct dyes. One or more dyes from the group Basic Yellow 87, Basic Yellow 57, Basic Orange 31, Basic Red 51, Basic Red 76, Basic Violet 2, Basic Violet 14, Basic Blue 7, Basic Blue 26, Basic Blue 99, Basic Brown 16, Basic Brown 17, HC Blue 16 and Cationic Blue 347 show particularly good compatibility.

Especially preferred additional cationic direct dyes are the azo dyes Basic Orange 31 and Basic Red 51.

For Basic Red 51, the dye is 2-[((4-dimethylamino) phenyl) azo]-1,3-dimethyl-1H-imidazolium chloride with CAS number 77061-58-6, commercially available, for example, under the trade names MIP RED 2985, RED (MIP 2985), MIP 2985 or VIBRACOLOR® Ruby Red.

Basic Orange 31 is the dye 2-[(4-amino-phenyl) azo]-1, 3-dimethyl-1H-imidazolium chloride with CAS number 97404-02-9, commercially available, for example, under the trade name of MIP Orange 3100, MIP 3100, Orange (MIP 3100), VIBRACOLOR® Flame Orange, or COLIPA B118.

It has proven particularly advantageous if the composition also contains Basic Orange 31 and Basic Red 51.

In addition, anionic direct dyes may be present, which are known under the International names or trade names of Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromophenol blue and tetrabromophenol blue.

These agents may also be used together with oxidation dyeing agents. Such oxidation dyeing agents additionally contain at least one oxidation dye precursor, preferably at least one oxidation dye precursor of the developer type and at least one oxidation dye precursor of the coupler type. Particularly suitable oxidation dye precursors of the developer type are selected from at least one compound from the group of p-phenylenediamine, p-toluylenediamine, 2-(2-hydroxyethyl)-p-phenylenediamine, 2-(1,2-dihydroxyethyl)-p-phenylenediamine, N, N-bis (2-hydroxyethyl)-p-phenylenediamine, 2-methoxymethyl-p-phenylenediamine, N-(4-amino-3-methylphenyl)-N-[3-(1H-imidazol-1-yl) propyl] amine, N, N'-bis (2-hydroxyethyl)-N, N'-bis-(4-aminophenyl)-1,3-diamino-propane-2-ol, bis-(2-hydroxy-5-amino-phenyl) methane, 1,3-bis (2,5-diaminophenoxy) propan-2-ol, N, N'-bis (4-aminophenyl)-1,4-diazacycloheptane, 1, 10-bis (2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl) phenol, 4-amino-2-(diethylaminomethyl) phenol, 4,5-diamino-1-(2-hydroxyethyl) pyrazole, 2,4,5,6-tetraaminopyrimidine, 4-hydroxy-2, 5,6-triaminopyrimidine, 2-hydroxy-4,5,6-triaminopyrimidine, 2,3-diamino-6,7-dihydro-1H, 5H-pyrazolo [1,2-a] pyrazol-1-one and the physiologically tolerated salts thereof.

Particularly suitable oxidation dye precursors of the coupler type are selected from the group of 3-Aminophenol, 5-Amino-2-methylphenol, 3-Amino-2-chlor-6-methylphenol, 2-Hydroxy-4-aminophenoxyethanol, 5-Amino-4-chlor-2-methylphenol, 5-(2-Hydroxyethyl)-amino-2-methylphenol, 2,4-Dichlor-3-aminophenol, 2-Aminophenol, 3-Phenylendiamin, 2-(2,4-Diaminophenoxy)ethanol, 1,3-Bis(2,4-diaminophenoxy)propan, 1-Methoxy-2-amino-4-(2-hydroxyethylamino)benzol, 1,3-Bis(2,4-diaminophenyl) propan, 2,6-Bis(2'-hydroxyethylamino)-1-methylbenzol, 2-({3-[(2-Hydroxyethyl)amino]-4-methoxy-5-methylphenyl}amino)ethanol, 2-({3-[(2-Hydroxyethyl) amino]-2-methoxy-5-methylphenyl}amino)ethanol, 2-({3-[(2-Hydroxyethyl)amino]-4,5-dimethylphenyl}amino) ethanol, 2-[3-Morpholin-4-ylphenyl)amino]ethanol, 3-Amino-4-(2-methoxyethoxy)-5-methylphenylamin, 1-Amino-3-bis-(2-hydroxyethyl)aminobenzol, Resorcin, 2-Methylresorcin, 4-Chlorresorcin, 1,2,4-Trihydroxybenzol, 2-Amino-3-hydroxypyridine, 3-Amino-2-methylamino-6-methoxypyridin, 2,6-Dihydroxy-3,4-dimethylpyridin, 3,5-Diamino-2,6-dimethoxypyridin, 1-Phenyl-3-methylpyrazol-5-on, 1-Naphthol, 1,5-Dihydroxynaphthalene, 2,7-Dihydroxynaphthalene, 1,7-Dihydroxynaphthalene, 1,8-Dihydroxynaphthalene, 4-Hydroxyindol, 6-Hydroxyindol, 7-Hydroxyindol, 4-Hydroxyindolin, 6-Hydroxyindolin, 7-Hydroxyindolin or mixtures of these compounds or their physiologically compatible salts.

The other direct dyes, developer and coupler components are used, preferably in a proportion of from about 0.0001 to about 5.0 wt. %, particularly from about 0.001 to about 3.5 wt. %, based on the ready-to-apply agent, in each case. Developer and coupler components are generally used in more or less molar quantities to one another. Even though molar use has proven to be appropriate, a certain excess of individual oxidation dye precursors is not disadvantageous. This means that the developer components and coupler components may be contained a molar ratio of from about 1:0.5 to about 1:3, and specifically of from about 1:1 to about 1:2.

If coloring using the non-ionic direct dyes and oxidative brightening of the keratinous fibers is not performed in a single step, the agents also contain an oxidant, preferably hydrogen peroxide and/or one of its fixed addition agents to organic or inorganic compounds.

In one embodiment, hydrogen peroxide is used as an aqueous solution. The concentration of this hydrogen peroxide solution is determined on the one hand by legal requirements and, on the other hand, by the desired effect; from about 6 to about 12 wt. % solutions in water are generally used. Appropriate ready-to-use agents are exemplified by the fact that, relative to the total weight of the application-ready agent, they contain from about 0.5 to about 20 wt. %, preferably from about 1 to about 12.5 wt. %, particularly from about 2.5 to about 10 wt. % and particularly preferably from about 3 to about 6 wt. % of hydrogen peroxide, each calculated based on the total weight of the agent. To achieve a greater lightening and bleaching effect, the agent can contain at least one sodium peroxide. Suitable sodium peroxides are inorganic peroxy compounds, preferably selected from the group of ammonium peroxodisulfate, alkali metal peroxodisulfates, ammonium peroxomonosulfate, alkali metal peroxomonosulfates, alkali metal peroxodiphosphates, and alkaline earth metal peroxides. Particularly preferred are peroxodisulphates, specifically ammoniumperoxodisulfate, potassium peroxodisulfate and sodiumperoxodisulfate.

In a further embodiment, an agent exemplified by the fact that it also contains at least one persulfate from the ammoniumperoxodisulfate, potassiumperoxodisulfate and sodiumperoxydisulfate group.

The persulfates are contained in the agent in a volume of from about 0.5 to about 20 wt. %, preferably from about 1 to about 12.5 wt. %, particularly from about 2.5 to about 10 wt. % and particularly preferably from about 3 to about 6 wt. %, relative to the total weight of the ready to use agent.

Ammoniumperoxodisulfate (or ammonium persulfate) is a compound of the formula $(NH_4)_2S_2O_8$. Potassiumperoxodisulfate (or potassium persulfate) is a compound of the formula $K_2S_2O_8$. Sodiumperoxydisulfate (or sodium persulfate) is a compound of the formula $Na_2S_2O_8$.

In principle, the agent can contain one or more zwitterionic and/or amphoteric, anionic, cationic or non-ionic surfactants. If the agent contains amphoteric and/or zwitterionic surfactants, the content of anionic and cationic surfactants in the agent should preferably be as low as possible.

The amphoteric surfactants are divided into ampholytic/amphoteric surfactants and zwitterionic surfactants. Ampholytic/amphoteric surfactants are surface active compounds that contain both acid (for example, —COOH or —$SC_3H$ groups) and also alkaline hydrophilic groups (for example, amino groups) and have acidic or alkaline behavior depending on the condition. Zwitterionic surfactants are specialist surfactants that carry both a negative and a positive charge in the same molecule.

Examples of preferred zwitterionic surfactants are betaines, the N-alkyl-N, N-dimethylammoniumglycinates, N-Acylaminopropyl-N, N-dimethylammoniumglycinate and the 2-alkyl-3-carboxymethyl-3-hydroxyethyl-imidazolines, each having 8 to 24 carbon atoms in the alkyl group.

Examples of preferred ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case from about 8 to 24 carbon atoms in the alkyl group.

Other preferred amphoteric and/or zwitterionic surfactants are surfactants with the following formulas (III) and/or (IV).

In another particularly preferred embodiment, there is an agent that is exemplified as containing at least one compound of formula (III) or (IV) formula as an amphoteric and/or zwitterionic surfactant,
COOH

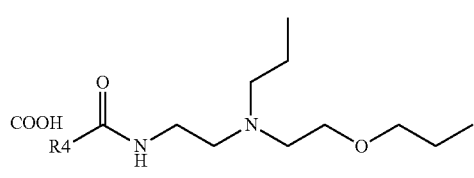
(III)

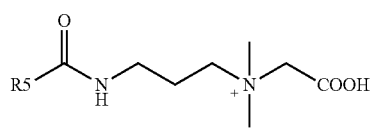
(IV)

where
R4, R5 are independent of one another for a saturated or unsaturated branched or unbranched $C_8$-$C_{24}$alkyl group.

One or more amphoteric or zwitterionic surfactants may be contained in a total volume of from about 0.1 to about 4.0 wt. %, preferably from about 0.2 to about 2.5 wt. %, more preferably from about 0.4 to about 1.8 wt. %, and particularly preferably from about 0.6 to about 0.9 wt. %—calculated based on the total weight of the agent in each case.

It can also prove beneficial if the agents contain non-ionic surfactants. Preferred non-ionic surfactants are alkyl polyglycosides as well as alkylene oxide binding agents to fatty alcohols and fatty acids with from 2 to 30 moles of ethylene oxide per mole of fatty alcohol or fatty acid.

Preparations with outstanding properties are also obtained if they contain fatty acid esters of ethoxylated glycerol as nonionic surfactants.

The non-ionic surfactants can be used in volumes from about 0.1 to about 45 wt. %, preferably from about 1 to about 30 wt. % and especially preferably from about 1 to about 15 wt. %, based on the total quantity of the ready-to-use agent.

By using one or more non-ionic direct dyes in agents containing a total of one or more polyols of at least about 0.1 wt. %, intense colors with exceptionally high shine can be obtained on keratinous fibers.

The addition of the usual state of the art shine-producing ingredients is therefore not required. For example, state-of-the-art technology indicates that certain oils can produce a shine. In contrast to the polyols used, it is also known that oils build up on the keratinous fibers, load the fibers and can therefore give them an oily appearance. In another particularly preferred embodiment, it is therefore preferable to use no oils from the group of fatty acid triglycerides, silicone oils and hydrocarbons in the agent. With the agent, it is possible to generate a shine despite not using these substances, and the keratinous fibers are not so loaded, do not appear greasy, and the hairstyle also does not lose volume.

The total content of the oils contained in the agent from the group of fatty acid triglycerides, silicone oils and hydrocarbons—in relation to the total weight of the agent—should preferably be at a value below about 1.0 wt. %, particularly below about 0.25% by weight or more preferably below about 0.1 wt. % and particularly preferably below about 0.05 wt. %.

An oil in this context refers to a hydrophobic compound that is liquid at 20° C., which favors solubility in water of less than about 1.0, preferably less than about 0.1 g per L (g of oil per liter of water).

The ready-to-use agents can contain adjuvants and additives.

Color processes on keratinous fibers are typically in the slightly acidic to alkaline range, preferably in the slightly acidic to slightly alkaline environment. To protect the keratinous fibers and also the skin as much as possible, setting too high a pH value is however not desirable. In principle, the pH value of the agent may be between about 1 and about 12. The pH-value should preferably be in the range of from about 1.0 to about 8.5, preferred from about 2.0 to about 8.0, more preferably from about 3.5 to about 7.0 and especially preferred from about 4.0 to about 6.9. The pH values are values that were measured at a temperature of 20° C., for example, with a glass electrode.

The preferred alkalizing media used to set the preferred pH value are ammonia, alkanolamines, basic amino acids and inorganic alkalinization media. Preferred inorganic alkalizing media are magnesium carbonate, sodium hydroxide, potassium hydroxide, sodium silicate and sodium silicate, applicable, organic alkalizing can be selected preferably from monoethanolamine, 2-amino-2-methylpropanol and triethanolamine. The basic amino acids that can be used as alkalizing agents are preferably selected from the group that is formed of arginine, lysine, ornithine, and histidine, especially arginine. The acidulents suitable for adjusting the pH-value are organic acids such as citric acid, acetic acid, ascorbic acid, benzoic acid, lactic acid, malic acid and maleic acid, as well as mineral acids such as hydrochloric acid, sulfuric acid or phosphoric acid.

It is also beneficial if the coloring agents, especially if they also contain hydrogen peroxide, contain at least one stabilizer or chelating agent. Particularly preferred stabilizers are phenacetin, alkali benzoates (sodium benzoate) and salicylic acid. Moreover, all state of the art complexing agents can be used, preferred complexing agents are nitrogen-containing polycarboxylic acids, particularly ethylene diamine tetraacetic acid (EDTA) and Ethylenediamine-"N", "N'"-disuccinic acid (EDDS), and phosphonates, particularly 1-hydroxy ethane-1,1-diphosphonate (HEDP) and/or diethylene triamine pentamethylene phosphonate (DTPMP) or their sodium salts.

The agent can also contain more active ingredients, adjuvants and additives, such as non-ionic polymers, cationic polymers, zwitterionic and amphoteric polymers, structurants, hair conditioning compounds, fiber structure enhancing agents, coloring substances for dyeing the agent, active anti-dandruff ingredients, amino acids, oligo-peptides, protein hydrolysates with an animal and/or vegetable base, light protection products, UV-blockers, active substances, vitamins, provitamins, vitamin precursors, plant extracts, fats, waxes, steeping and penetration substances, opacifiers, pearl shine concentrates, thickeners, pigments as well as propellants.

The specialist will select these other substances in accordance with the desired properties of the agent.

It has proven to be particularly advantageous if the agent also contains one or more $C_{12}$-$C_{30}$ fatty alcohols in a minimum volume of about 15.0 wt. %.

The agent preferably therefore contains one or more $C_{12}$-$C_{30}$ fatty alcohols in a total volume of at least about 15.0 wt. %. In this case, the calculation basis for the volume of polyols (b) is the total of all the polyols contained in the agent used in relation to the total volume of the agent.

According to the present disclosure, a $C_{12}$-$C_{30}$ fatty alcohol is a $C_{12}$-$C_{30}$ fatty alcohol, i.e. a saturated or unsaturated $C_{12}$ $C_{30}$ alkyl chain, which is substituted by a hydroxy group. The substitution of the alkyl chain by the hydroxy group can be done at the end of the alkyl chain, or even in the middle of the alkyl chain. It is preferable to substitute the (saturated or unsaturated) terminal alkyl chain by a hydroxy group.

The $C_{12}$-$C_{30}$ alkyl chain can be linear or branched.

Preferred $C_{12}$-$C_{30}$ fatty alcohols (d) are selected from the group of

Dodecyl alcohol, laurylalcohol (dodecan-1-ol)
Tetradecyl alcohol, myristyl alcohol (tetradecan-1-ol),
hexadecyl alcohol, cetyl alcohol, palmityl alcohol (hexadecan-1-ol),
Octadecyl alcohol, stearyl alcohol (octadecan-1-ol),
Oleyl alcohol ((9Z)-Octadec-9-en-1-ol),
Eicosan-1-ol (arachyl alcohol),
(9Z)-Eicos-9-en-1-ol (gadoleyl alcohol),
(5Z,8Z, 11Z, 14Z)-Eicosa-5,8,11,14-tetraen-1-ol (arachidonic alcohol),
Heneicosan-1-ol (heneicosyl alcohol),
Docosan-1-ol (Behenyl alcohol),
(13Z)-Docos-13-en-1-ol (erucyl alcohol) and/or
(13E)-Docosen-1-ol (brassidyl alcohol).

The use of mixtures of $C_{12}$-$C_{30}$ fatty alcohols, for example a mixture of $C_{12}$-$C_{16}$ fatty alcohols, $C_{16}$-$C_{18}$ fatty alcohols, $C_{20}$-$C_{22}$ fatty alcohols and $C_{12}$-$C_{18}$ fatty alcohols $C_{18}$-$C_{24}$ fatty alcohol, is also particularly preferred.

The $C_{12}$-$C_{30}$ fatty alcohols are preferred in a total volume of at least about 15.0 wt. % in the agent. A minimum volume of about 15.0 wt. % in this context means that 100 g of the agent contains a total quantity of at least about 15.0 g of one or more $C_{12}$-$C_{30}$ fatty alcohols. It is preferred that the total volume of the $C_{12}$-$C_{30}$ fatty alcohols is a maximum about 60.0 wt. %, more preferably about 30.0 wt. %.

The use of $C_{12}$-$C_{30}$ fatty alcohols leads to a further significant increase in the glossiness of the keratinous fibers. The best results can be obtained if one or more fatty alcohols are used in a total volume of from about 15.0 to about 60.0 wt. %, preferably from about 16.0 to about 40.0 wt. %. Particularly advantageous are volumes from about 17.0 to about 30.0 wt. %. Within the group of $C_{12}$-$C_{30}$ fatty alcohols, long-chain and short chain fatty alcohols can be distinguished. According to the present disclosure, short-chain fatty alcohols refer to fatty alcohols with from 12 to 16 carbon atoms. Long-chain fatty alcohols are fatty alcohols having at least 18 carbon atoms. Within the group of long-chain fatty alcohols, the fatty alcohols with a chain length of from 18 to 24 carbon atoms are particularly preferred.

A particularly advantageous solution of the stated goal has been found when the agents contain both short-chain and long-chain fatty alcohols in specific volume ranges.

Furthermore, hair-conditioning compounds may preferably be contained in the agents. Due to cationic or cationizable groups, for example, hair-conditioning compounds have a degree of substantivity to human hair, especially protonated amine groups or quaternary ammonium groups.

The agent can be used as a single component agent or as a multi-component agent, such as two-component agent or three-component agent and applied accordingly. Separation into multicomponent systems is ideal in cases where incompatibilities of the ingredients can be expected or feared; the agent to be used in such systems is created by the consumer immediately prior to use by mixing the components.

The agent for changing the color of keratinous fibers is always understood as a ready-to-use agent.

If the agent is provided to the user in the form of a single component agent, the ready-to-use agent does not have to be created, but can be taken directly from the container in which it was formulated and applied to the keratinous fibers. However, bleaching agents are typically two-component products, in which an oxidant-containing component (A1) is mixed shortly before application with an (alkalization) agent (A2) and this ready for use mixture is applied to the hair.

In this case, the agent is a ready-to-use agent, prepared just before application by mixing (A1) and (A2).

In this case, the nonionic direct dye (a) and/or the polyol (b) will be prepared in component (A1) (that is, together with the oxidant) or in component (A2) (together with the alkalizing agent).

It is also possible that the ready-to-use agent is produced on the human hair shortly before use by mixing three components, wherein component (A1) contains at least one nonionic direct dye (a), component (A2) at least one first oxidizing agent (e.g. hydrogen peroxide)

and component (A3) at least one second oxidizing agent (for example, one or more peroxodisulfate salts). In this case, the polyol (b) may be prepared in component (A1) and/or (A2) and/or (A3).

As already described above, the shine of keratinous fibers while dyeing of the fibers and also the color uptake of the dye(s) can be increased by combining one or more non-ionic direct dyes with at least one polyol. Improved gray coverage is also achieved.

Another object of the present disclosure is therefore the use of a composition containing, in a cosmetic carrier, (a) at least one non-ionic direct dye and (b) at least about 0.1 wt. %—in relation to the entire agent—of one or several polyols.

increase the gloss on hair and/or increase the color uptake of dyes and/or increase the gray coverage when dyeing human hair.

With respect to other preferred embodiments of the present disclosure, the agents mentioned in the present disclosure apply mutatis mutandis.

The agent that is the subject of the present disclosure can be used in procedures for dyeing human hair.

Another object of the present disclosure is therefore a method to increase hair gloss and/or to increase the color uptake of dyes increase gray coverage when dyeing human hair using an agent contained in a cosmetic carrier, (a) a nonionic direct dye and (b) at least about 0.1 wt. %—in relation to the entire agent—of one or several polyols is applied to the hair.

With respect to further preferred embodiments of the method, the agents and applications mentioned in the present disclosure apply mutatis mutandis.

EXAMPLES

The following formulations have been produced. Unless otherwise noted, the stated volumes are each by weight percentage and the active substance used.

|  | V1 | E1 | E2 |
|---|---|---|---|
| $C_{12}$-$C_{18}$ fatty alcohol | 3.0 | 3.0 | 3.0 |
| $C_{16}$-$C_{12}$ fatty alcohol | 8.0 | 8.0 | 8.0 |
| Propylparaben | 0.15 | 0.15 | 0.15 |
| Methyl paraben | 0.4 | 0.4 | 0.4 |
| Cocoamphodipropionate, disodium salt | 0.64 | 0.64 | 0.64 |
| Ceteareth-20 | 2.0 | 2.0 | 2.0 |
| HC Blue 15 | 0.2 | 0.2 | 0.2 |
| 1.3 butylene glycol | — | 4.0 | — |
| PEG-8 | — | — | 4.0 |
| Tetrasodium ethylene diamine tetra acetate ($Na_4EDTA$) | 0.002 | 0.5 | 0.5 |
| Monoethanolamine | 0.005 | 0.005 | 0.005 |
| Sodium silicate | 0.19 | 0.19 | 0.19 |
| Hydroxy ethane 1.1 diphosphonic acid | 0.24 | 0.24 | 0.24 |
| Water | ad 100 | ad 100 | ad 100 |

In each case, 90 g of color formulations V1, E1 and E2, and 10 g of a propane-butane mixture, were placed in two separate chambers of a foam dispenser.

1. Color Uptake

Before the dyeing process, strands of hair (Kerling 10-0) were measured colorimetrically (Spectralflasch SF 450 colorimetry apparatus from Datacolor). Subsequently, the application-ready color formulations prepared as described above were applied to the strands of hair and left there at room temperature for 30 minutes. The strands of hair were then rinsed thoroughly and dried in the air stream. After dyeing and drying, the hair tresses were measured again by colorimetry. According to the following formula, the color difference (ΔE) between undyed and dyed strands was calculated:

$$\Delta E = \sqrt{(Lv-Ln)^2 + (av-an)^2 + (bv-bn)^2}$$

Lv, av, bv colorimetric values before dyeing
Ln, an, bn colorimetric values after dyeing

| Determining the color uptake assets |  | L | a | b | ΔE |
|---|---|---|---|---|---|
| Kerling 10-0 | before dyeing | 58.14 | 7.16 | 24.90 |  |
| Dyeing with V1 | After dyeing | 33.21 | −16.75 | −7.56 | 47.4 |
| Dyeing with E1 | After dyeing | 31.04 | −14.93 | −15.32 | 53.3 |
| Dyeing with E2 | After dyeing | 32.02 | −15.38 | −15.44 | 53.1 |

The greater the color difference between the undyed and dyed strands, the stronger the color uptake resulting from the dye. When applying the formulations E1 and E2, a significantly more intense color result when compared to the comparative formulation V1 was obtained in each case.

2. Gray Coverage

The gray coverage can be determined by the following procedure: A gray and a non-gray hair strand is measured colorimetrically before dyeing and after dyeing (to determine the Lab values). These values are used to calculate the gray coverage index in %.

The higher the gray coverage index, the better the gray coverage.

Undyed buffalo abdominal hair (yak hair, representing gray hair) and undyed Kerling Euro natural hair 10-0 (Kerling) were measured colorimetrically. Then, the previously produced color formulations were each applied to each of the two types of hair (liquor ratio 4:1,4 g of cream per g of hair) and left for 30 minutes. The strands of hair were then rinsed and dried. The dyed and dried hair strands were measured a second time by colorimetry. The gray coverage index was determined according to the following formula:

$$GAI = \left(1 - \frac{dE(dY-dH)}{dE(uY-dH)}\right) * 100$$

GCI: Gray coverage index (in percent)

dY: dyed buffalo abdominal hair dH: colored pigmented hair (Kerling Euro natural hair 10-0)

uY: undyed buffalo abdominal hair (gray hair)

The values shown in the ΔE GAI-formula are determined using the following formula:

$$\Delta E = \sqrt{(L-L')^2 + (a-a')^2 + (b-b')^2}$$

For the L, a and b values, the values indicated in each case in the GCI formula (Lab values of dyed buffalo abdominal hair, undyed buffalo abdominal hair, and dyed pigmented hair) can be used. The higher the gray coverage index, the better the gray coverage of a formulation.

|  | L | a | b | GCI: |
|---|---|---|---|---|
| dH: colored pigmented hair (Kerling Euro natural hair 10-0) | 58.14 | 7.16 | 24.90 | ... |
| uY: undyed buffalo belly hair | 74.75 | −1.00 | 10.90 | ... |
| Buffalo belly hair, dyed using V1 | 55.75 | −16.75 | −16.29 | 49.75 |
| Kerling 10-0, dyed using V1 | 33.21 | −16.75 | −7.56 |  |
| Buffalo belly hair, dyed using E1 | 53.94 | −17.48 | −20.80 | 55.18 |
| Kerling 10-0, dyed using E1 | 31.04 | −14.93 | −15.32 |  |
| Buffalo belly hair, dyed using E2 | 53.72 | −15.36 | −14.08 | 58.36 |
| Kerling 10-0, dyed using E2 | 32.02 | −15.38 | −15.44 |  |

The results show that dyeing agents E1 and E2 with a polyol result in improved gray coverage.

| | V2 | E3 |
|---|---|---|
| VP/VA Polymer | 1.9 | 1.9 |
| Polyquaternium-11 | 0.53 | 0.53 |
| Polyquaternium-4 | 0.30 | 0.30 |
| Cetrimonium Chloride | 0.27 | 0.27 |
| Quaternium-52 | 0.21 | 0.21 |
| PEG-40 Hydrogenated Castor Oil | 0.43 | 0.43 |
| Panthenol | 0.15 | 0.15 |
| HC Blue 12 | 0.2 | 0.2 |
| 1,2-Propylenglycol | — | 1.9 |
| Phenoxyethanol | 0.01 | 0.01 |
| Sodium benzoate | 0.32 | 0.32 |
| KOH | 0.005 | 0.005 |
| Caprylyl glycol | 0.01 | 0.01 |
| Citric acid | 0.02 | 0.02 |
| Lactic acid | 0.07 | 0.07 |
| Perfume | 0.15 | 0.15 |
| Glycerol | 0.21 | 0.21 |
| Water | ad 100 | ad 100 |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:

1. Agent for coloring keratinous fibers, included in a cosmetic carrier and comprising:
   (a) at least one non-ionic direct dye comprising HC Blue 15,
   and
   (b) at least about 0.1 wt. %—in relation to the entire agent—of 1,3-butylene glycol and/or PEG-8.

2. An agent according to claim 1, further comprising a polyol selected from the group of polyhydric $C_2$-$C_9$ alkanols with two to six hydroxyl groups, polyethylene glycols with from 3 to 20 ethylene oxide units, and mixtures thereof.

3. An agent according to claim 2, wherein the polyol is selected from the group of 1,2-propylene glycol, glycerol, PEG-3, PEG-4, PEG-5, PEG-6, PEG 7, and mixtures thereof.

4. An agent according to claim 2, wherein the polyol is 1,2-propylene glycol.

5. An agent according to claim 1, wherein the 1,3-butylene glycol and/or PEG-8—in relation to the entire agent—is present in an amount of from about 1.0 to about 20.0 wt %.

6. An agent according to claim 1 further comprising an additional non-ionic direct dye selected from the group of HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, 1,4-diamino-2-nitrobenzene, 2-amino-4-nitrophenol, 1,4-Bis(2-Hydroxyethyl)-amino-2-nitrobenzene, 3-Nitro-4-(2-hydroxyethyl)aminophenol, 2-(2-hydroxyethyl)amino-4,6-dinitrophenol, 4-[(2-hydroxyethyl)amino]-3-nitro-1-methyl benzene, 1-Amino-4-(2-hydroxyethyl)amino-5-chloro-2-nitrobenzene, 4-Amino-3-nitrophenol, 1-(2'-Ureidoethyl)amino-4-nitrobenzene, 2-[(4-Amino-2-nitrophenol)amino]benzoic acid, 4-[(3-hydroxypropyl)amino]-3-nitrophenol, 4-Nitro-o-phenylenediamine, 6-Nitro-1,2,3,4-tetrahydrochinoxaline, 2-hydroxy-1,4-naphthoquinone, picramic acid and their salts, 2-Amino-6-chloro-4-nitrophenol, 4-(Ethylamino)-3-nitrobenzoic acid and 2-Chlor-6-ethylamino-4-nitrophenol, and mixtures thereof.

7. An agent according to claim 1, further comprising HC Blue 12.

8. An agent according to claim 1, wherein the HC Blue 15 is present in a total quantity of from about 0.01 to about 5.0 wt. %, in relation to the total weight of the agent.

9. An agent according to claim 1, further comprising Basic Red 51 and Basic Orange 31 separate from the HC Blue 15.

10. An agent according to claim 1, further comprising one or more $C_{12}$-$C_{30}$ fatty alcohols in a minimum volume of about 15.0 wt. %.

11. A method comprising dying human hair using an agent included in a cosmetic carrier and comprising:
   a) at least one non-ionic direct dye comprising HC Blue 15,
   and
   b) at least about 0.1 wt. %—in relation to the entire agent—of 1,3-butylene glycol and/or PEG-8.

12. An agent according to claim 1, wherein the 1,3-butylene glycol and/or PEG-8—in relation to the entire agent—is present in an amount of from about 2.0 to about 10.0 wt. %.

13. An agent according to claim 1, wherein the HC Blue 15 is present in a total quantity of from about 0.075 to about 0.2 wt. %—in relation to the total weight of the agent.

14. An agent according to claim 1, further comprising 1,2-propylene glycol, wherein the 1,2-propylene glycol along with the 1,3-butylene glycol and/or PEG-8 are present—in relation to the entire agent—in an amount of from about 2.0 to about 10.0 wt. %.

15. An agent according to claim 1, further comprising 1,2-propylene glycol wherein the 1,2-propylene glycol along with the 1,3-butylene glycol and/or PEG-8 are present—in relation to the entire agent—in an amount of from about 2.0 to about 10.0 wt. %, wherein the nonionic direct dye further comprises HC Blue 12, and wherein the nonionic direct dyes are present in a total quantity of from about 0.075 to about 0.2 wt. %—in relation to the total weight of the agent.

16. An agent according to claim 15, further comprising Basic Red 51 and Basic Orange 31 separate from the HC Blue 15 and HC Blue 12.

17. An agent according to claim 15, further comprising one or more $C_{12}$-$C_{30}$ fatty alcohols in a minimum volume of 15.0 wt. %.

18. An agent according to claim 1 comprising the 1,3-butylene glycol and free of the PEG-8 and any other polyols.

19. An agent according to claim 1 comprising the PEG-8 and free of the 1,3-butylene glycol and any other polyols.

* * * * *